United States Patent
Farris et al.

[11] Patent Number: 6,131,736
[45] Date of Patent: Oct. 17, 2000

[54] PACKAGING DEVICE FOR AN INTERLABIAL ABSORBENT ARTICLE

[75] Inventors: Diane Dunn Farris, West Chester; Alicia Mary Hall; Thomas Ward Osborn, III, both of Cincinnati, all of Ohio

[73] Assignee: The Procter & Gamble Company, Cincinnati, Ohio

[21] Appl. No.: 09/340,912

[22] Filed: Jun. 28, 1999

[51] Int. Cl.7 .................................................. A61F 13/15
[52] U.S. Cl. ..................................... 206/440; 604/385.1
[58] Field of Search ................................. 206/438, 440, 206/441, 484, 804; 604/385.1, 386, 387, 358, 904

[56] References Cited

U.S. PATENT DOCUMENTS

| | | | |
|---|---|---|---|
| 3,062,371 | 11/1962 | Patience | 206/440 |
| 3,938,659 | 2/1976 | Wardwell | 206/440 |
| 3,973,567 | 8/1976 | Srinvasan et al. | 206/440 |
| 4,648,867 | 3/1987 | Conner et al. | 604/904 |
| 5,771,524 | 6/1998 | Woods et al. | 604/385.1 |
| 5,916,205 | 6/1999 | Olson et al. | 604/904 |
| 5,964,689 | 10/1999 | McFall et al. | 604/385.1 |
| 6,010,001 | 1/2000 | Osborn, III | 206/440 |

*Primary Examiner*—David T. Fidei
*Assistant Examiner*—Luan K. Bui
*Attorney, Agent, or Firm*—Theodore P. Cummings; Matthew P. Fitzpatrick; Steven W. Miller

[57] ABSTRACT

The invention provides an individual package in combination with an absorbent interlabial device. The package has a longitudinal axis, a top portion, a bottom portion positioned oppositely to the top portion, a first surface and a second surface. The package may be folded about the longitudinal axis to form two halves or it may be formed from one more sheets fitted together to form the package. The package may be re-sealable. An absorbent interlabial device is positioned within the package. The absorbent interlabial device is readily retrievable from the package such that a user neither touches nor contaminates the absorbent portion of the absorbent interlabial device with any part of her hand prior to the use and in using the absorbent interlabial device.

24 Claims, 4 Drawing Sheets

PACKAGING DEVICE FOR AN INTERLABIAL ABSORBENT ARTICLE

FIELD OF THE INVENTION

This invention relates to individual packages for absorbent devices that are worn interlabially by female wearers for catamenial purposes, incontinence protection, or both.

BACKGROUND OF THE INVENTION

All manner and variety of absorbent articles configured for the absorption of body fluids such as menses, urine and feces are, of course, well known. With respect to feminine protection devices, the art has offered two basic types; sanitary napkins have been developed for external wear about the pudendal region while tampons have been developed for internal wear within the vaginal cavity for interruption of menstrual flow therefrom. Such tampon devices are disclosed in U.S. Pat. No. 4,412,833, entitled "Tampon Applicator," issued to Weigner, et al. on Nov. 1, 1983, and U.S. Pat. No. 4,413,986, entitled "Tampon Assembly With Means For Sterile Insertion", issued to Jacobs on Nov. 8, 1983.

Hybrid devices that attempt to merge the structural features of the sanitary napkins and the tampons into a single device have also been proposed. Such hybrid devices are disclosed in U.S. Pat. No. 2,092,346, entitled "Catamenial Pad," issued to Arone on Sep. 7, 1937, and U.S. Pat. No. 3,905,372, entitled "Feminine Hygiene Protective Shield," issued to Denkinger on Sep. 16, 1975. Other less intrusive hybrid devices are known as labial or interlabial sanitary napkins and are characterized by having a portion which at least partially resides within the wearer's vestibule and a portion which at least partially resides external of the wearer's vestibule. Such devices are disclosed in U.S. Pat. No. 2,662,527, entitled "Sanitary Pad," issued to Jacks on Dec. 15, 1953, and U.S. Pat. No. 4,631,062, entitled "Labial Sanitary Pad," issued to Lassen, et al. on Dec. 23, 1986.

Interlabial pads have the potential to provide even greater freedom from inconvenience because of their small size and reduced risk of leakage. Numerous attempts have been made in the past to produce an interlabial pad which would combine the best features of tampons and sanitary napkins while avoiding at least some of the disadvantages associated with each of these types of devices. Examples of such devices are described in U.S. Pat. No. 2,917,049 issued to Delaney on Dec. 15, 1959, U.S. Pat. No. 3,420,235 issued to Harmon on Jan. 7, 1969, and U.S. Pat. No. 4,595,392 issued to Johnson, et al. on Jun. 17, 1986. A commercially available interlabial device is FRESH 'N FIT® PADETTE® interlabial product that is marketed by Athena Medical Corp. of Portland, Org. and described in U.S. Pat. Nos. 3,983,873 and 4,175,561 issued to Hirschman on Oct. 5, 1976 and Nov. 27, 1979, respectively.

Absorbent interlabial articles need to be hygienically stored from the time of their manufacture until the article is used. This is a particular concern with respect to maintaining a sanitary environment prior to placement or insertion. That is, a need exists to hygienically store an individual absorbent article while being transported to prevent transferring unsanitary particles to the pudendal or vaginal area.

The packaging for the commercially available FRESH 'N FIT® PADETTE® interlabial product is made from a coated paper sheet that is wrapped around the product and sealed on the transverse ends and along the longitudinal edges. The transverse ends and longitudinal edges of the product are sometimes sealed with an adhesive and are then crimped or knurled together. An example of packaging for an interlabial pad is shown in U.S. Pat. No. 4,743,245 entitled "Labial Sanitary Pad" that issued to F. O. Lassen, et al. on May 10, 1988. However, there are drawbacks to these interlabial product packages.

One important drawback is that packages for interlabial products do not provide a means for users of interlabial products to preserve hygiene when removing a product from a protective package or inserting an interlabial product into the folds of the skin. The lack of hygiene in restrooms, the need to touch the doors of non-hygienic restrooms, and the necessity to touch themselves while inserting the device may result in the possibility of infection. In addition, when inserting the device during menstruation, it is desirable to keep the user's hands free from soiling. Therefore, the consumer needs an individual package that will hygienically protect an interlabial device during its removal from a package and simultaneously during insertion thereof.

Other packages for sanitary articles are described in U.S. Pat. No. 3,062,371 entitled "Internally Sterile Composite Package" that issued to D. Patience on Nov. 6, 1962 and U.S. Pat. No. 3,698,549 entitled "Packages for Small Articles" that issued to J. A. Glassman on Oct. 17, 1972. The Patience patent describes a package that is opened by folding back a panel from the package and removing its content by using sterile forceps. The Glassman patent describes a package that has internal pockets for holding flat articles such as gauze dressings or surgical sponges. The package is opened and exposes separate pockets for removal of individual articles.

Although the packages described in the Patience patent, the Glassman patent, the package used with the PADETTE® product, and the package described in the Lassen patent protect the enclosed article, the package does not aid in the hygienic removal, insertion and placement of the absorbent interlabial device or provide a barrier to prevent the wearer's hand from touching the product or the wearer's body. Additionally, neither package described above provides a convenient means for users of interlabial products to dispose of the packaging after the product has been used. Conventionally, users would dispose of the packaging by placing the product in her purse, throwing it on the bathroom floor, placing it in a trash receptacle for sanitary products, or placing the packaging in a trash receptacle outside of the bathroom stall. Some users may attempt to flush packages whether they are or are not designed to be flushed, and regardless of whether they are dispersible in water or biodegradable.

Packages for tampons are described in U.S. Pat. No. 3,135,262 entitled "Tampon" that, issued to W. Kobler, et al. on Jun. 2, 1964 and U.S. Pat. No. 5,180,059 entitled "Package of a Sanitary Tampon" that issued to S. Shimatani and K. Shimatani on Jan. 19, 1993. The Kobler patent describes a package that when unwrapped, forms what Kobler describes as an umbrella to cover the user's hands. Because of the shape of the tampon (the height of the tampon is considerably greater than the tampon's longitudinal dimension), the package must be considerably longer than the tampon to encircle the user's hand when opened. When the package is opened, the material that forms the shield is large and would be an impediment to proper placement. Additionally, the package in the Kobler patent does not completely seal all parts of the product inside the package creating the potential for contamination. Specifically, the tear cord used to break the band that holds the package onto the tampon must be touched by the user. The same cord, when the tampon is in use, then resides in the vaginal region that is sensitive to contamination.

The Shimatani patent describes a package that comprises packing sheets superimposed on another to enclose the tampon to create a shield when inserting the tampon. This patent fails to provide a sterile environment because it, too, does not seal all parts of the product inside the package that should be protected from contamination or prevent the user from touching parts that should maintain sterility. Additionally, the stiffness of the Shimatani package would not provide comfort for the user when inserting the article.

The packages for the Kobler and Shimatani patents are tall and circular in shape. The Kobler and Shimatani packages may be suitable in packaging articles that have a height greater than its longitudinal dimension, however, with smaller articles such as an interlabial product where its longitudinal dimension is greater than the article's height, such a package would not be feasible. The package of the present invention is flat in comparison. Also, the package of the present invention differs from the Kobler and Shimatani packages because they are not flushable or biodegradable.

Therefore, it is an object of the present invention to provide a hygienic individual package for an interlabial device.

It is another object of the present invention to provide an individual package for an interlabial device that facilitates hygienic removal of the device from the package.

It is another object of the present invention to provide an individual package for an absorbent interlabial device that prevents the hand from directly contacting the part of the device that is worn interlabially.

It is also an object of the present invention to provide disposal of a used absorbent interlabial device within its original package, both of which are preferably biodegradable and/or flushable together.

It is yet another object of the present invention to provide a hygienic individual package for an absorbent interlabial device that is separately flushable and biodegradable.

It is a further object of the invention herein to provide an individual package that facilitates ease of removal of an interlabial device without the opportunity of contamination.

These and other objects of the present invention will become more readily apparent when considered in reference to the following description and when taken in conjunction with the accompanying drawings.

SUMMARY OF THE INVENTION

Accordingly, the invention provides a re-sealable individual package for an absorbent interlabial device. The re-sealable individual device comprises a package having a longitudinal axis, a top portion, a bottom portion positioned oppositely to the top portion, a first surface and a second surface. The first surface of the package is also the internal surface thereof and the second surface of the package is also the external surface thereof In one embodiment herein, the package comprises a single sheet that is folded about the longitudinal axis to form two halves. The package is sealed permanently on at least two sides. At least one side of the package is sealed non-permanently and is re-sealable. One-half of the internal surface of the folded package is connected to and faces toward the other half of the internal surface of the folded package.

An absorbent interlabial device is positioned within the package. The absorbent interlabial device has a longitudinal axis, and an absorbent portion having a first surface and a second surface. The absorbent interlabial device also preferably has a grasping portion for readily retrieving the absorbent interlabial device from the package. The grasping portion prevents a user from either touching or contaminating the first surface of the absorbent portion of the absorbent interlabial device with any part of her hand. Thus, when the package is opened, the absorbent interlabial device is positioned within the package such that the grasping portion, which is connected adjacent to the second surface of the absorbent portion, faces upwardly towards the package opening and is therefore available to be immediately grasped while the first surface of the absorbent portion faces inwardly away from the package opening. The first surface of the absorbent portion may preferably comprise a topsheet.

Preferably, the re-sealable individual package further comprises a contaminant impermeable portion or backsheet attached to the second surface of the absorbent portion of the absorbent interlabial device. Thus, when a user removes the absorbent interlabial device by pulling the grasping portion and therefore the device out of the package, a user's fingers can never contaminate the absorbent portion because the contaminant impermeable portion stands as a barrier therebetween. In practice, the contaminant impermeable portion of the absorbent interlabial device at last partially covers the fingers on the user's hand grasping the grasping portion to remove the absorbent interlabial device from the package. Furthermore, in a preferred embodiment herein, the absorbent portion will tend to fold down towards a user's hand to provide a barrier against contamination. The absorbent portion will tend to fold downwardly along the longitudinal axis of the absorbent interlabial device.

Preferably, the length and width dimensions of the contaminant impermeable portion are greater than the length and width dimensions of the absorbent portion of the absorbent interlabial device. The contaminant impermeable portion is attached to the second surface of the absorbent portion of the absorbent interlabial device.

The absorbent interlabial device is preferably positioned within the package such that the absorbent interlabial device is folded about its longitudinal axis. In this configuration, the first surface of the absorbent portion of the absorbent interlabial device is positioned adjacent to the internal surface of the package. Preferably, the absorbent interlabial device is flushable and/or biodegradable. Also preferably, the package is flushable and/or biodegradable. The absorbent interlabial device and package may be either flushed and/or biodegradable together.

After its use, the absorbent interlabial device may be placed back into the package and re-sealed for disposal purposes. At least one side of the re-sealable individual package may be re-sealed once the absorbent interlabial device is removed from and/or placed back into the package. More specifically, the package may be sealed on at least one side by a re-sealing member. Preferably, the re-sealing member is positioned at least partially on the top portion of the package. In one embodiment herein, the re-sealing member is positioned on one of the halves of the internal surface of the package. In another embodiment, the re-sealing member may be positioned at least partially on a package external surface alone or in combination with the package internal surface.

Of course, the re-sealing member may be positioned on both of the halves of the internal surface of the package as well as positioned at least partially on the package external surfaces alone or in combination with the package internal surfaces. The re-sealing member may be selected from the group consisting of re-fastenable tape, thermal bonds, pressure sensitive tapes, pressure sensitive glues and combinations thereof.

In another embodiment herein, the re-sealable individual package further comprises a disruptive member for opening the re-sealable individual package. The disruptive member is positioned adjacent to the top portion of the re-sealable individual package. The disruptive member extends partially along the top portion of the re-sealable individual package. Preferably, the disruptive member extends substantially along the top portion of the re-sealable individual package. More specifically, the disruptive member may comprise an opening device for opening the package. The opening device may comprise a pull-string, a line of weakness and/or perforations. Herein, the individual package is not necessarily re-sealable.

In another embodiment herein, a re-sealable individual package for an absorbent interlabial device is provided that comprises two sheets of like size and geometry that are attached or secured to one-another, a longitudinal axis, a top portion, a bottom portion positioned oppositely to the top portion, a first surface and a second surface. The first surface of the package is also the internal surface thereof and the second surface of the package is also the external surface thereof.

The package is substantially sealed about the longitudinal axis and sealed on at least three sides, at least one sealed side of the package being re-sealable and two other sides being at least partially permanently sealed. The internal surface further comprises a first internal surface and a second internal surface facing toward the first internal surface.

An absorbent interlabial device is positioned in the package, the absorbent interlabial device having a longitudinal axis, an absorbent portion having a first surface and a second surface. The absorbent interlabial device is readily retrievable from the package such that a user neither touches nor contaminates the first surface of the absorbent portion of the absorbent interlabial device with any part of her hand; this is especially true where a grasping portion has been affixed adjacent to the second surface of the absorbent interlabial device.

In yet another embodiment herein, an individual package for an absorbent interlabial device is provided that comprises a package having a first surface and a second surface. The first surface of the package is also the internal surface thereof and the second surface of the package is also the external surface thereof. The package is sealed on at least three sides.

An absorbent interlabial device is positioned within the package. The absorbent interlabial device has a longitudinal axis, an absorbent portion having a first surface and a second surface. The absorbent interlabial device is readily retrievable from the package such that a user neither touches nor contaminates the first surface of the absorbent portion of the absorbent interlabial device with any part of her hand.

BRIEF DESCRIPTION OF THE DRAWINGS

While the specification concludes with claims particularly pointing out and distinctly claiming the subject matter which is regarded as forming the present invention, it is believed that the invention will be better understood from the following descriptions which are taken in conjunction with the accompanying drawings in which like designations are used to designate substantially identical elements, and in which:

DETAILED DESCRIPTION OF THE INVENTION

Figure 3:
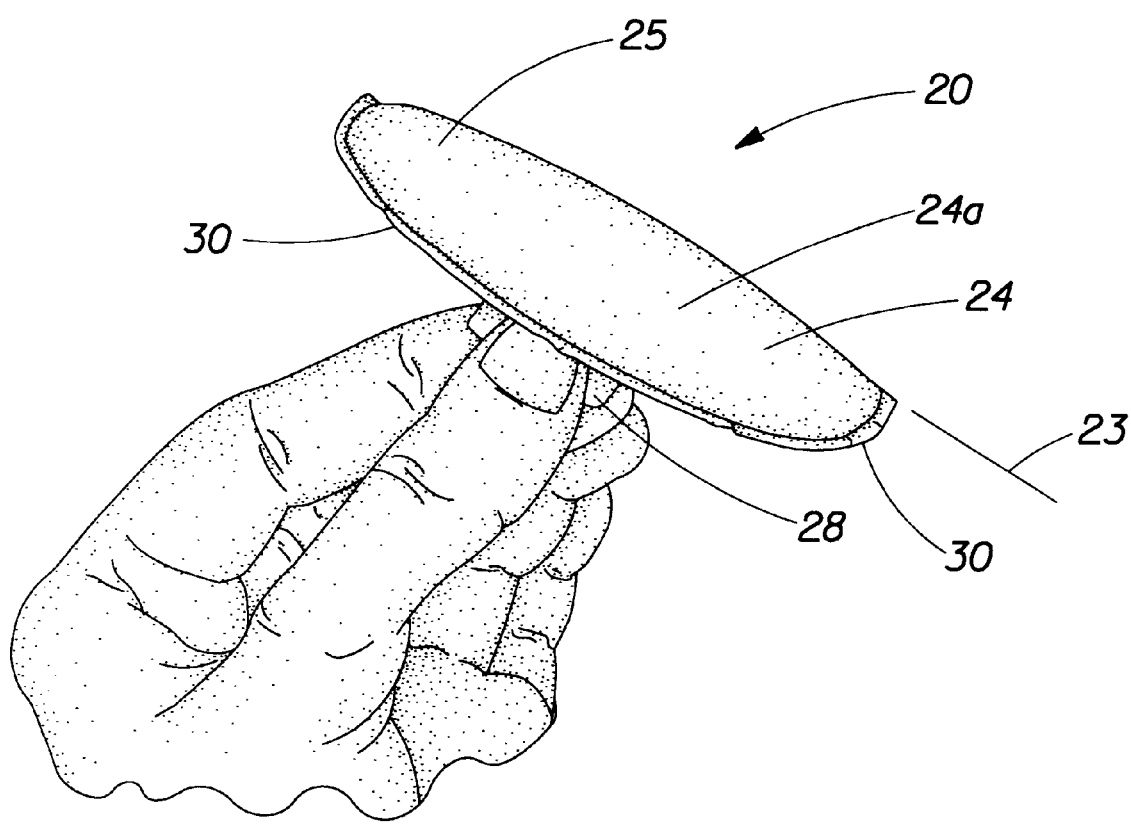
FIG. 3 is a perspective view of the absorbent interlabial device being held by a user.
Figure 4:
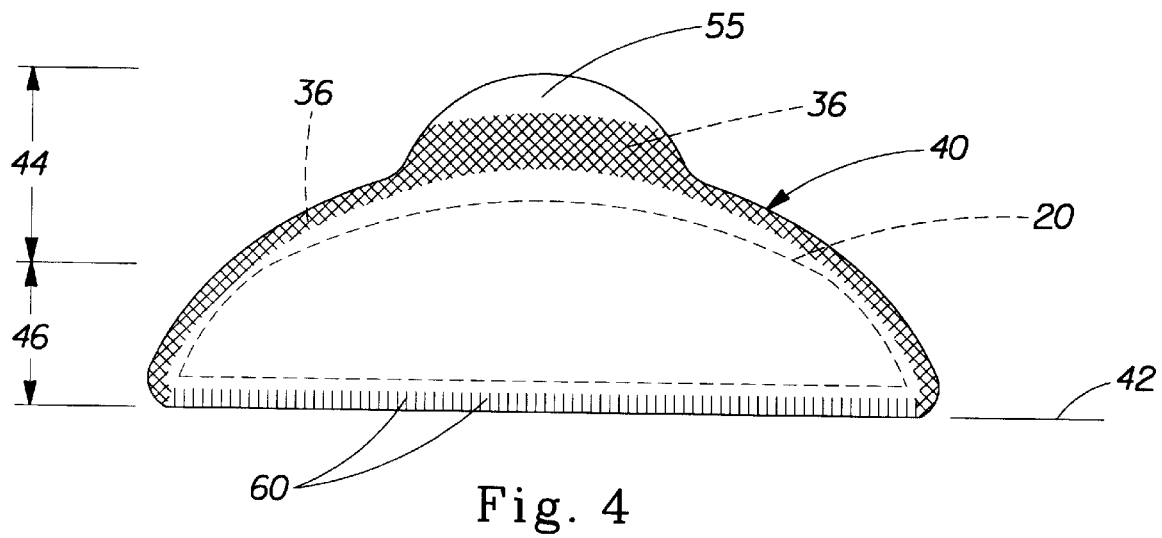
FIG. 4 is a side view of an alternative embodiment of the individual package with the absorbent interlabial device residing therein.
Figure 5:
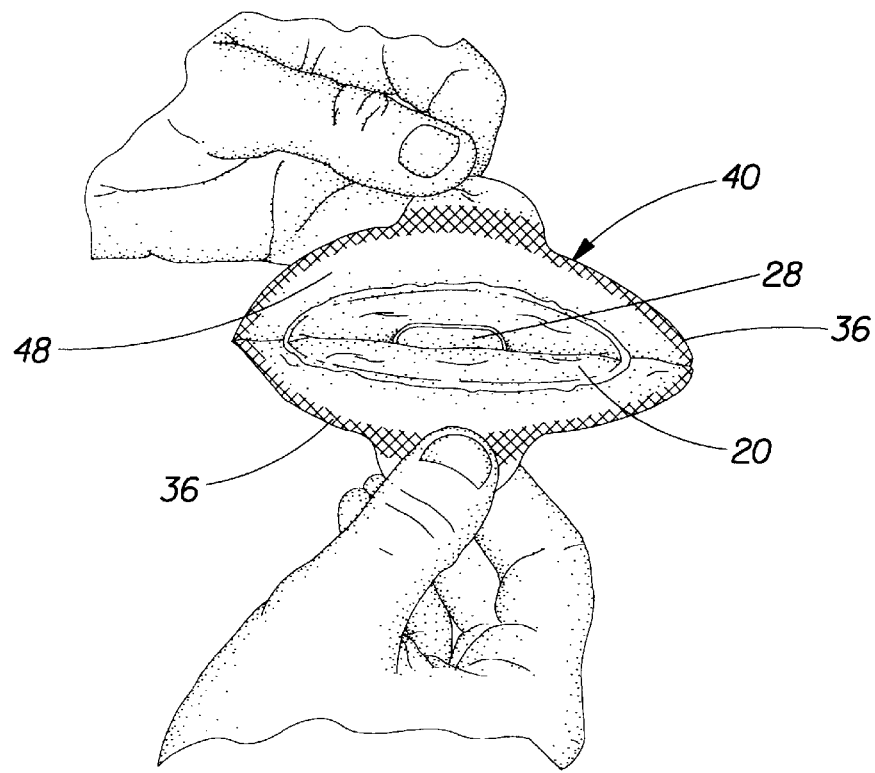
FIG. 5 is a perspective view of the embodiment of FIG. 4 of the individual package with the absorbent interlabial device residing therein.

As used herein, the term "absorbent interlabial device" or "interlabial device" refers to a structure that has at least some absorbent components, and is specifically configured to reside at least partially within the interlabial space of a female wearer during use. One such interlabial device is shown in FIG. 3. Preferably, more than half of the entire absorbent interlabial device 20 resides within such interlabial space, more preferably substantially the entire absorbent interlabial device 20 resides within such interlabial space, and most preferably the entire absorbent interlabial device 20 resides within such interlabial space of a female wearer during use.

As used herein, the term "interlabial space" refers to that space in the pudendal region of the female anatomy that is located between the inside surfaces of the labia majora extending into the vestibule. Located within this interlabial space are the labia minora, the vestibule and the principal urogenital members including the clitoris, the orifice of the urethra, and the orifice of the vagina. Standard medical authorities teach that the vestibule refers to the space bounded laterally by the inside surfaces of the labia minora and extending interiorly to the floor between the clitoris and the orifice of the vagina. Therefore, it will be recognized that the interlabial space as defined above may refer to the space between the inside surfaces of the labia majora, including the space between the inside surfaces of the labia minora also known as the vestibule. The interlabial space for purposes of the present description does not extend substantially beyond the orifice of the vagina into the vaginal interior.

The term "labia" as used herein refers generally to both the labia majora and labia minora. The labia terminate anteriorly and posteriorly at the anterior commissure and the posterior commissure, respectively. It will be recognized by those skilled in the art that there is a wide range of variation among women with respect to the relative size and shape of labia majora and labia minora. For purposes of the present description, however, such differences need not be specifically addressed. It will be recognized that the disposition of the absorbent interlabial device into the interlabial space of a wearer as defined above will require placement between the inside surfaces of the labia majora without regard to the precise location of the boundary between the labia majora and the labia minora for a particular wearer. For a more detailed description of this portion of the female anatomy, attention is directed to *Gray's Anatomy,* Running Press 1901 Ed. (1974), at 1025–1027.

Figure 1:
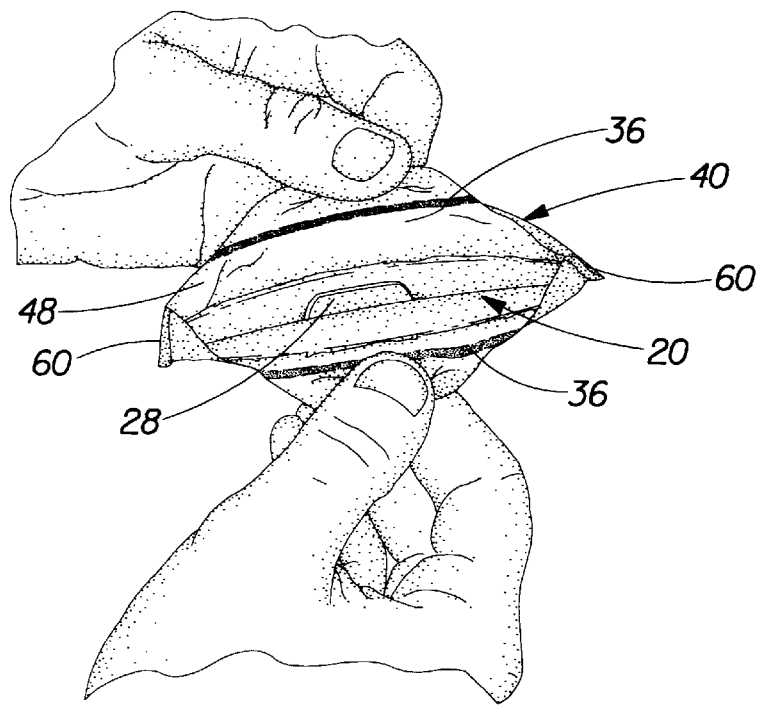
FIG. 1 is a perspective drawing showing an opened individual package with an absorbent interlabial device residing therein.
Figure 2:
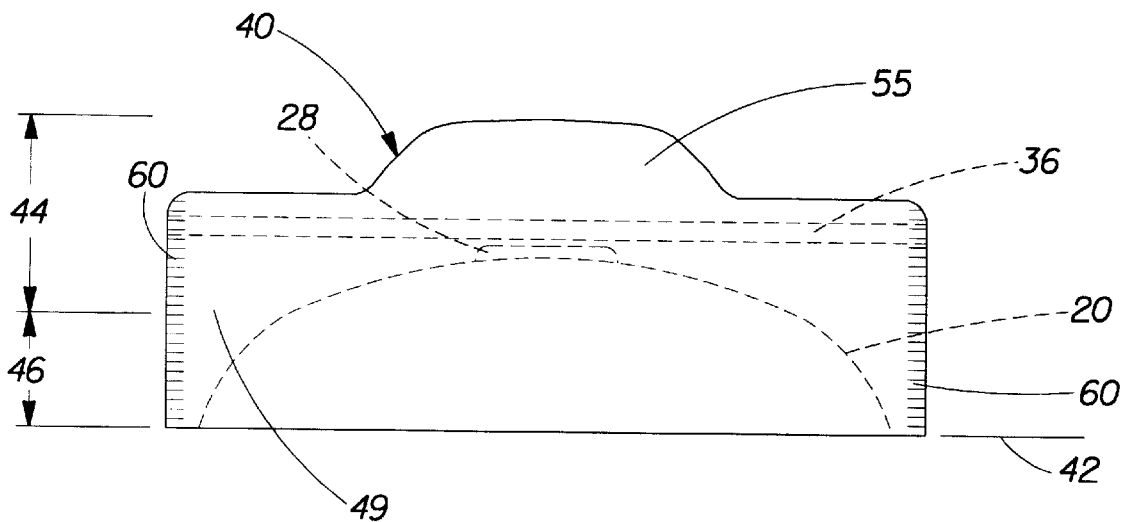
FIG. 2 is a side view of an embodiment of the individual package with the absorbent interlabial device residing therein.

As is shown in FIGS. 1 and 2, the invention provides a re-sealable individual package 40 for an absorbent interlabial device 20 having a longitudinal axis 42, a top portion 44, a bottom portion 46 positioned oppositely to the top portion 44, a first surface 48 and a second surface 49. The first surface 48 of the package 40 is also the internal surface 48 thereof and the second surface 49 of the package 40 is also the external surface 49 thereof. In one embodiment herein, the package 40 comprises a single sheet that is folded about the longitudinal axis 42 to form two halves. The package 40 is sealed on at least three sides. At least one sealed side of the package 40 is re-sealable. One-half of the internal surface of the folded package 40 faces toward the other half of the internal surface 48 of the folded package 40.

In addition, opening members 55 are preferably positioned along the top of the package 40 and within the top portion 44 (FIG. 2). As is shown in FIG. 1, a user may grasp the opening members 55 to pull apart the package 40 to reveal absorbent interlabial device 20.

In FIG. 1, an absorbent interlabial device 20 is shown positioned within the package 40. The absorbent interlabial device 20 has a longitudinal axis 23, an absorbent portion 24 having a first surface 25 and a second surface 26 (not shown), and preferably a grasping portion 28 used for readily retrieving the absorbent interlabial device 20 from the package 40 such that a user neither touches nor contaminates the first surface 25 of the absorbent portion 24 of the absorbent interlabial device 20 with any part of her hand (FIG. 3). Thus, when the package 40 is opened, the absorbent interlabial device 20 is positioned within the package 40 such that the grasping portion 28, which is connected adjacent to the second surface 26 (not shown) of the absorbent portion 24, faces outwardly towards the package 40 opening, while the first surface 25 of the absorbent portion 24 faces inwardly away from the package 40 opening. The first surface 25 of the absorbent portion 24 may comprise a topsheet.

Preferably, the absorbent interlabial device 20 further comprises a contaminant impermeable portion 30 or backsheet 30 which is attached to the second surface 26 of the absorbent portion 24 of the absorbent interlabial device 20. Thus, when a user removes the absorbent interlabial device 20 by pulling the grasping portion 28 and therefore the device 20 out of the package 40, a user's fingers can never contaminate the first surface 25 of the absorbent portion 24 because the contaminant impermeable portion 30 stands as a barrier therebetween. The contaminant impermeable portion 30 prevents the absorbent portion 24 from being contaminated by liquids, particulate matter or semi-solids. In practice, a contaminant impermeable portion 30 herein would at least partially cover the fingers on a user's hand grasping the grasping portion 28 to remove the absorbent interlabial device 20 from the package 40 (FIG. 3).

Preferably, as is shown in FIG. 3, the length and width dimensions of the contaminant impermeable portion 30 are greater than the length and width dimensions of the absorbent portion 24 of the absorbent interlabial device. The contaminant impermeable portion 30 is attached to the second surface 26 of the absorbent portion 24 of the absorbent interlabial device 20.

The absorbent interlabial device 20 is preferably positioned within the contaminant impermeable portion 30 such that the absorbent interlabial device 20 is folded about its longitudinal axis 22. In this configuration, the first surface 25 of the absorbent portion 24 of the absorbent interlabial device 20 is positioned adjacent to the internal surface 48 of the package 40. Preferably, the absorbent interlabial device 20 is flushable and/or biodegradable. Also preferably, the package 40 is flushable and/or biodegradable. Also preferably, both the absorbent interlabial device 20 and the package 40 are flushable and/or biodegradable together.

After its use, the absorbent interlabial device 20 may be placed back into the package 40 and re-sealed for disposal purposes. At least one side of the re-sealable individual package 40 may be re-sealed once the absorbent interlabial device 20 is removed from and/or placed back into the package 40. More specifically, the package 40 may be sealed on at least one side by a re-sealing member 36 (FIG. 1). Preferably, the re-sealing member 36 is positioned at least partially on the top portion 44 of the package 40. In one embodiment herein, the re-sealing member 36 is positioned on one of the halves of the internal surface 48 of the package 40. In another embodiment, the re-sealing member 36 may be positioned at least partially on the package 40 external surface alone or in combination with the package 40 internal surface 48.

Of course, the re-sealing member 36 may be positioned on both of the halves of the internal surface 48 of the package 40 as well as positioned at least partially on the package external surfaces 49 alone or in combination with the package internal surfaces 48. The re-sealing member 36 may be selected from the group consisting of re-fastenable tape, thermal bonds, pressure sensitive tapes, pressure sensitive glues and combinations thereof. In fact any suitable means for providing a re-sealing member 36 are readily foreseeable by one skilled in the art.

As is shown in FIGS. 1, 2, 4, and 6A–7, the package 40 further comprises permanent seals 60. By the term "permanent seals", it is meant herein seals that bind portions of the package 40 together in a substantially permanent and un-resealable manner. The permanent seals 60 generally extend along the sides of a package 40 but may extend only partially along those sides. If the permanent seals 60 extend only along a portion of the package sides, then those portions not permanently sealed will be sealed by one or more re-sealing members 36. Typically, permanent seals 60 herein are formed from heat seals, crimps, pressure seals and/or any other suitable sealing method known in the art; since the method used to permanently sealing portions of the package forms no part of the invention, any suitable sealing method may be used. Suitable methods for frangibly sealing the edges of a package are described in U.S. Pat. No. 4,556,146 issued to Swanson, et al., U.S. Pat. No. 5,181,610 issued to Quick, and U.S. Pat. No. 5,462,166 issued to Minton, et al, each of which patents is hereby incorporated by reference herein.

Figure 6A:
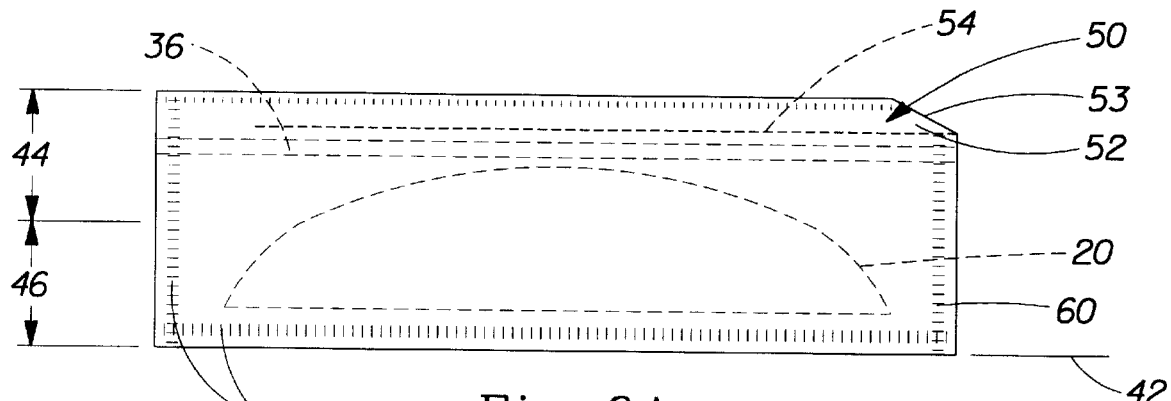
FIG. 6A is a side view of an alternative embodiment of the individual package with the absorbent interlabial device residing therein.
Figure 6B:
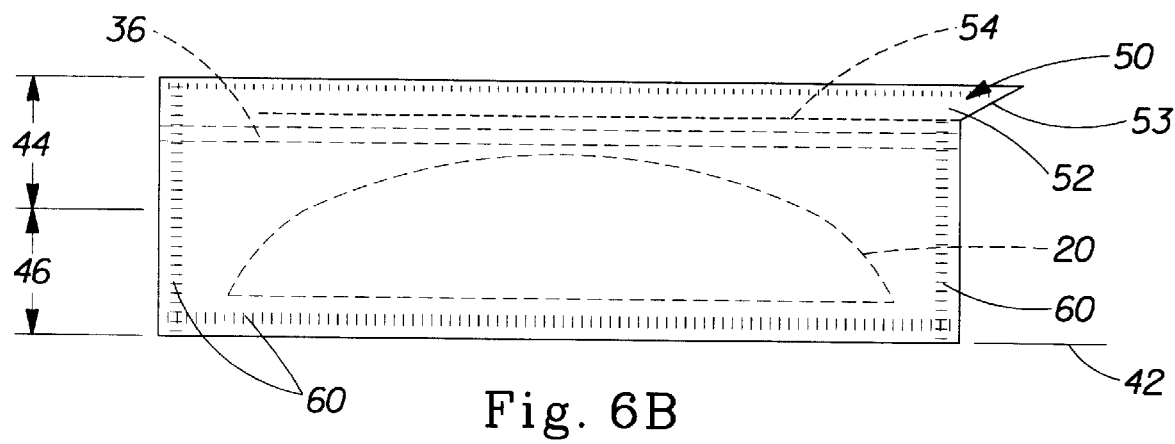
FIG. 6B is a side view of an alternative embodiment of the individual package with the absorbent interlabial device residing therein.

In another embodiment herein, the individual package 40 further comprises a disruptive member 50 or tear member 50 for opening the individual package 40 (FIGS. 6A–6B). In this context, the individual package 40 may be either re-sealable via the existence of one or more re-sealing members 36 placed within or on the package 40 or the package 40 may not be re-sealable at all. The disruptive member 50 is positioned within the top portion 44 of the package 40 and includes a tear member 52 and a tear strip 54. The disruptive member 50 extends partially along the top portion 44 of the package 40. Preferably, the disruptive member 50 extends substantially along the top portion 44 of the package 40.

Figure 7:
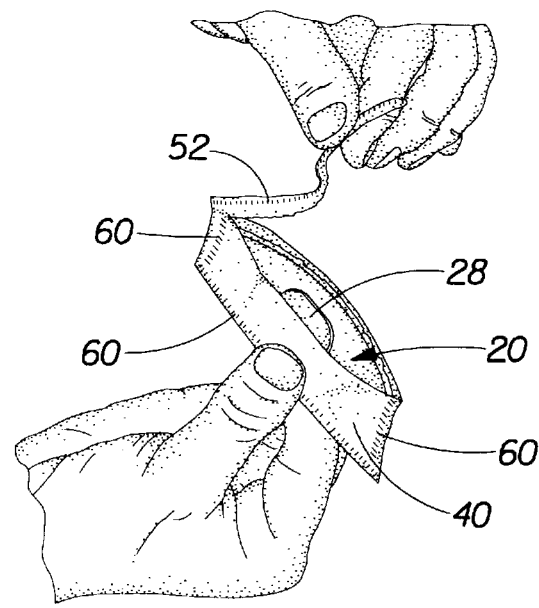
FIG. 7 is a perspective view of the opening of one of the individual packages shown in FIG. 6A or 6B.

In practice, a user grasps the angled portion 53 of the tear member 52 and pulls the tear member 52 along the line of the tear strip 54, which is preferably a weakened and/or perforated portion. Once pulled, the tear member 52 should readily disrupt the tear strip 54 such that the package 40 is opened along the entire length of the tear strip 54. Once opened, the interlabial package 20 should be readily retrievable and the grasping portion 28 evident and easily grasped (FIG. 7).

In another embodiment herein, the individual package 40 preferably comprises a line of weakness which can be in the form of perforations 54 that are positioned along the upper portion 44 of the package 40 (FIGS. 6A–6B). In other alternate embodiments, the line of weakness can be in the form of a score line, such as that made by laser scoring. The individual package 40 preferably also has a tear strip or string that generally extends along and in the direction of the perforations 54. The individual package 40 is opened by using the tear string to break the perforations 54 along a significant portion of the periphery of the individual package 40.

The absorbent interlabial device 20 or interlabial device 20 or device 20 should be of a suitable size and shape that allows at least a portion thereof to fit comfortably within the wearer's interlabial space and to cover the wearer's vaginal orifice, and preferably also the wearer's urethra. The interlabial device 20 at least partially blocks, and more preferably completely blocks and intercepts the flow of menses, urine, and other bodily exudates from the wearer's vaginal orifice and urethra.

The interlabial device 20 is preferably provided with sufficient absorbency to absorb and retain the exudates discharged from the wearer's body. The capacity of the product, however, is dependent at least partially upon the physical volume of the absorbent interlabial device 20, particularly the central absorbent portion 22 thereof.

The central absorbent portion 22 preferably has a capacity of at least about 1 g of 0.9% by weight saline solution, and may have a capacity of up to about 30 grams by using absorbent gels or foams that expand when wet. Capacities may typically range from about 2 to about 10 grams, for saline. Those skilled in the art will recognize that the capacity for absorption of body exudates such as menses will typically be smaller than the capacities given above for absorption of saline. Since the interlabial space can expand, larger volumes can be stored in the interlabial space, if the fluid is stored as a gel, which adjusts to the body pressures. Additionally, if the absorbent interlabial device 20 does not reside completely within the wearer's interlabial space, some of the absorbed exudates may be stored externally to the wearer's interlabial space.

The absorbent portion 24 of the interlabial device 20 may comprise any suitable type of absorbent structure that is capable of absorbing and/or retaining liquids (e.g. menses and/or urine). The absorbent portion 24 may be manufactured in a wide variety of shapes. Non-limiting examples include ovoid, trapezoidal, rectangular, triangular, cylindrical, hemispherical or any combination of the above. The absorbent portion 24 may, likewise, be manufactured and from a wide variety of liquid-absorbent materials commonly used in absorbent articles such as comminuted wood pulp that is generally referred to as airfelt. Examples of other suitable absorbent materials include cotton; creped cellulose wadding; meltblown polymers including coform; chemically stiffened, modified or cross-linked cellulosic fibers; synthetic fibers such as crimped polyester fibers; peat moss; tissue including tissue wraps and tissue laminates; absorbent foams; absorbent sponges; superabsorbent polymers; absorbent gelling materials; or any equivalent material or combinations of materials, or mixtures of these. Preferred absorbent materials comprise folded tissues, woven materials, nonwoven webs, needle punched rayon, and thin layers of foam. The absorbent portion 24 may comprise a single material or a combination of materials, such as a wrapping layer surrounding a central wadding comprised of a different absorbent material.

In the embodiment shown in FIG. 3, the absorbent portion 24 is formed of a soft absorbent material such as rayon fibers or other suitable natural or synthetic fibers or sheeting. The absorbent portion 24 shown in FIG. 3 is generally of an ovoid cross sectional shape. The absorbent portion 24 of the embodiment shown in FIG. 3 comprises a first surface 24A with a larger transverse sectional dimension relative to that of the second surface 24B (not shown). The first surface 24A is preferably integral with the second surface 24B. In less preferred embodiments, however, the first surface 24A and second surface 24B may comprise separate elements joined together by any suitable means know in the art.

The interlabial device 20 in any of the embodiments shown in the drawings may comprise other optional components. For example, the interlabial device 20 may comprise a topsheet 25 (not shown) positioned over and joined to all or a portion of the body facing surface of the device 20 and/or a backsheet 38 positioned over and joined to all or a portion of its back surface. Preferably, if a topsheet 25 and/or a backsheet 38 is used, these components are joined to at least a portion of the absorbent portion 24. In an alternative embodiment, the absorbent portion 24 could be at least partially wrapped by a topsheet 25.

If a topsheet is used, the topsheet should be compliant, soft feeling, and non-irritating to the wearer's skin. Further, the topsheet should be liquid pervious permitting liquids (e.g., menses and/or urine) to readily penetrate through its thickness. A suitable topsheet may be manufactured from a wide range of materials such as woven and nonwoven materials comprised of natural fibers (e.g., wood or cotton fibers), synthetic fibers (e.g., polymeric fibers such as polyester, rayon, polypropylene, or polyethylene fibers) or from a combination of natural and synthetic fibers. Other woven and nonwoven materials may include polymeric materials such as apertured formed thermoplastic films, apertured plastic films, and hydroformed thermoplastic films; porous foams; reticulated foams; reticulated thermoplastic films; and thermoplastic scrims.

The topsheet may comprise an apertured formed film. Apertured formed films are pervious to body exudates and, if properly apertured, have a reduced tendency to allow liquids to pass back through and rewet the wearer's skin. Thus, the surface of the formed film which is in contact with the body remains dry, thereby reducing body soiling and creating a more comfortable feel for the wearer. Suitable formed films are described in U.S. Pat. No. 3,929,135, entitled "Absorptive Structures Having Tapered Capillaries", which issued to Thompson on Dec. 30, 1975; U.S. Pat. No. 4,324,246 entitled "Disposable Absorbent Article Having A Stain Resistant Topsheet", which issued to Mullane, et al. on Apr. 13, 1982; U.S. Pat. No. 4,342,314 entitled "Resilient Plastic Web Exhibiting Fiber-Like Properties", which issued to Radel, et al. on Aug. 3, 1982; U.S. Pat. No. 4,463,045 entitled "Macroscopically Expanded Three-Dimensional Plastic Web Exhibiting Non-Glossy Visible Surface and Cloth-Like Tactile Impression", which issued to Ahr, et al. on Jul. 31, 1984; and U.S. Pat. No. 5,006,394 "Multilayer Polymeric Film" issued to Baird on Apr. 9, 1991. The preferred topsheet for the interlabial device is the formed film described in one or more of the above patents and marketed on sanitary napkins by The Procter & Gamble Company of Cincinnati, Ohio as the "DRI-WEAVE" topsheet.

If such a formed film is used in an interlabial device, the body surface of the formed film topsheet is preferably hydrophilic so as to help liquid to transfer through the topsheet faster than if the body surface was not hydrophilic so as to diminish the likelihood that menstrual fluid will flow off the topsheet rather than flowing into and being absorbed by the absorbent portion 24. In a preferred embodiment, surfactant is incorporated into the polymeric materials of the formed film topsheet. Alternatively, the body surface of the topsheet can be made hydrophilic by treating it with a surfactant such as is described in U.S. Pat. No. 4,950,254 issued to Osborn.

Where a backsheet is used, the backsheet 38 could be impervious or semi-pervious to liquids (e.g., menses and/or urine) and is preferably flexible. As used herein, the term "flexible" refers to materials which are compliant and will readily conform to the general shape and contours of the human body. The backsheet 38 prevents the exudates absorbed and contained in the absorbent portion 24 from wetting articles which contact the absorbent interlabial device 20 such as the wearer's undergarments. The backsheet also assists the absorbent portion 24 in preventing the wearer's body from being soiled by exudates. Additionally, use of the backsheet may provide an improved surface for the wearer to grasp between the fingers as the absorbent interlabial device 20 is inserted, or as the device is optionally removed with the fingers. Lastly, the backsheet protects the absorbent portion 24 from contamination by a user's fingers during placement of the absorbent interlabial device.

The backsheet 38 may comprise a woven or nonwoven material, polymeric films such as thermoplastic films of polyethylene or polypropylene, or composite materials such as a film-coated nonwoven material. Preferably, the backsheet 38 is a film having a thickness of from about 0.012 mm (0.5 mil) to about 0.051 mm (2.0 mils). An exemplary polyethylene film is manufactured by Clopay Corporation of Cincinnati, Ohio, under the designation P18-0401. The backsheet may permit vapors to escape from the central absorbent portion 22 (i.e., breathable) while still preventing exudates from passing through the backsheet. The backsheet 38 is preferably biodegradable and/or flushable.

Whether re-sealable or un-resealable, the individual package 40 encloses the absorbent interlabial device 20 to provide a sanitary environment. The package 40 should at least partially enclose the absorbent interlabial device 20, and preferably completely enclose the absorbent interlabial device 20. The package 40 comprises at least one sheet of flexible material. The sheets may come in various sizes and shapes, such sizes and shapes not limiting the scope of the invention. The package 40 can be folded about or wrapped around the absorbent interlabial device 20 in any suitable manner. In one embodiment herein, the package 40 is preferably folded about or wrapped around the absorbent interlabial device 20.

An advantage of the present invention is that it protects the user's fingers from touching either the interlabial device 20 as the device 20 is removed from the package 40. Another advantage of the present invention is that it provides a protective covering for the interlabial device 20 during transport or storage of the product. Maintaining a hygienic environment for the interlabial device before and during use is vital to prevent transferring unsanitary particles to the interlabial space.

Preferably, the package 50 has a thickness of from about 0.0127 mm (0.5 mil) to about 0.127 mm (5.0 mils). The package 50 may be made from plastic films, that may be thermoplastic, nonwoven materials, collagen films, paper tissues, or laminates of tissue and a film, nonwoven material and a film, or any of the foregoing types of material with a coating thereon. One embodiment of the present invention may be made from a low basis weight tissue that disintegrates in water. The low basis weight tissue can be made of carboxymethyl cellulose with wood pulp fibers and will disintegrate in water with a temperature of 75° F. (24° C.) in approximately 6 seconds; and disintegrate in water with a temperature of 50° F. in approximately 8 seconds. One such material is sold as DISSOLVO® WLD-35 water soluble purge dam material for gas-tungsten arc (TIG) welding by CMS Gilbreath Packaging Systems of Bensalem, Pa.

In addition, such low basis weight tissues may be combined with coatings or films like polyvinyl acetate (PVA), polyvinyl alcohol (PVOH), or methyl hydroxy propyl cellulose (MHPC) that also dissolve in water. One such material is sold as Mono-Sol® MC-8630 water soluble film by Chris Craft® Industrial Products, Inc., Gary, Ind. One preferred laminate material is made using a Hot Roll Laminator obtained from Cheminstruments by combining a 0.089 mm (3.5 mil) thick sheet of DISSOLVO® WLD-35 tissue with a 0.038 mm (1.5 mil) Mono-Sol® MC-8630 MHPC water soluble film. Laminating the tissue at a temperature between 344° F. (173° C.) to 366° F. (185° C.) and at a feed rate between 35 ft/min to 50 ft/min with the MHPC film produces a material 0.1 mm (4 mil) thick that is preferred for making the package of the present invention.

The laminated material has a basis weight of 93.6 g/m$^2$. The material will disintegrate in water with a temperature of 75° F. (24° C.) in approximately 6.1 seconds and 7.9 seconds in water with a temperature of 50° F. The average time for the laminated material to dissolve is approximately 17.3 seconds in water with a temperature 75° F. (24° C.) and 34.4 seconds in water with a temperature 50° F. (10° C.).

The tear resistance (tear strength) of the film is approximately 1575 g$_f$, while the tear resistance of the DISSOLVO® WLD-35 is approximately 25 g$_f$ in the direction of the process flow through a manufacturing line for making the paper, the machine direction (MD), and 25 g$_f$ in the direction perpendicular to the machine direction, the cross-machine direction (CD). The tear resistance of the laminated material is approximately 88 g$_f$ (MD), and 76.8 g$_f$ (CD). The tear strength of the laminate is significantly less than that of the film by itself. The increase in the tear strength when comparing the paper to the laminated material provides a stronger package that will not tear as easily as paper alone. The reduction in tear strength when comparing the film to the laminated paper and film enables the user to open the package with greater ease than if the package were made from the film alone. When the materials are laminated, the superior tear resistant properties of the film are compromised, yet the strength of the paper is significantly increased, providing an ideal package that is easily opened, yet strong enough to resist tearing from handling and transporting.

The laminated material, like a number of the other package materials identified above, also aids in heat sealing the package, provides a sanitary and moisture-free environment, and reduces noise associated with tearing paper when opening and carrying the package. The laminated material also produces a package that can be opened with or without a line of weakness.

The package 40 is preferably constructed of materials which are at least 70% biodegradable, more preferably at least 90% biodegradable, and/or which will fragment in water with agitation (as in a toilet). Preferably, the absorbent interlabial device 20 and the package 40 for the absorbent interlabial device 20 are both flushable separately or in combination, and when flushed the package or the combination of the absorbent interlabial product and the package will clear the toilet 80% of the time and biodegrade at least 95% of the time in a 28 Day Sludge Test. As used herein the terms "flushable and flushability" refer to a an article's ability to pass through typical commercially available U.S. household toilets and plumbing drainage systems without causing clogging or similar problems that can be directly associated with the physical structure of the article.

It is recognized, however, that there can be many differences between the various types of toilets available. Therefore, for the purposes of the appended claims, a test to determine the flushability of a catamenial product, such as an interlabial device, or the package of a catamenial product is set out in the TEST METHODS section of this specification.

In addition, numerous embodiments of the individual packages described herein are possible. For example, the package could be provided in other configurations while still performing the functions described herein. Further, the packaging materials described herein can be used with a variety of absorbent articles configured for the absorption of body fluids such as female or male incontinence products, tampons, or externally worn sanitary napkins where a hygienic environment is a paramount concern. For instance, the adhesive on sanitary napkins and/or the wing adhesive of winged sanitary napkins can be covered by cover strips made of such materials. Additionally, a package that serves as an individual package for a sanitary napkin such as that described in U.S. Pat. No. 4,556,146 entitled "Individually Packaged Disposable Absorbent Article" which issued to Swanson et al. on Dec. 3, 1985 could be provided that is made of such a material.

TEST METHODS

Flushability

Overview

As noted above, the terms "flushable or flushability" refer to a article's capacity to pass through typical commercially available household toilets and plumbing drainage systems without causing clogging or similar problems that can be directly associated with the physical characteristics of the article. For the purpose of the appended claims, absorbent articles, such as interlabial products and their packages are evaluated for flushability via relative ease of toilet bowl and trap evacuation and subsequent transport through a simulated plumbing system. The flushability of such articles and packages should be measured by the following test procedure.

The test procedure is designed to simulate two days of normal toilet usage for a family of 4 (2 men, 2 women). The test employs a flushing sequence to simulate the following conditions: male urination visits, female urination visits (including post urinary drying with tissue), disposal of the absorbent article or package with cleaning using tissue, and bowel movement visits. The amount of tissue to be used for each tissue flush is a normal loading of 2 strips of seven sheets. The normal loading is based on consumer research regarding typical habits and practices. The test is designed to simulate the conditions an article will encounter if it is flushed through a conventional toilet and into a municipal sewer or into a septic tank. Samples are evaluated for: 1) toilet bowl and trap clearance, 2) drain line blockage, and 3) disintegration during flushing.

Apparatus

An apparatus suitable for the flushability test is shown in plan view in FIG. 9. The apparatus includes:

a 3.5 gallon (13.2 liter) water saver siphon vortex toilet referred to as 210 (additional toilets can also be attached to the piping layout shown in FIG. 9 to evaluate the behavior of test samples using different flushing mechanisms such as commercial, pressure toilets);

approximately 59 feet (18 meters) of 4 inch (10 cm) inside diameter acrylic pipe (As can be seen from FIG. 9, the piping is assembled in roughly a square configuration having linear runs 211,213,215,217,219,221 approximately 10 feet (3 meters) long);

a cast iron tee 223 slightly downstream of the toilet 210 that is open to the atmosphere for venting;

five cast iron ninety degree elbows 212, 214, 216, 218, and 220;

a spike or snag 222 positioned vertically (FIG. 10) approximately 15 feet from the pipe's terminal end and approximately 1 inch (2.5 cm) long; and a screen 224 (No. 4 Tyler sieve) to capture solid effluent for evaluation of disintegration.

The apparatus used for this method is set up to be equivalent to ANSI Standard A112.19.2M-1990 for Vitreous China fixtures. The piping is plumbed to provide a drop of 0.25 inch per foot (2 centimeters/meter) of pipe length.

Materials

Tissue Product used in Test: Standard CHARMIN® toilet tissue manufactured by The Procter & Gamble Company of Cincinnati, Ohio.

Synthetic Fecal Material: Prepared according to the method described below

Test Flushing Sequence

The test flushing sequence, consisting of two routines, simulates 2 days of normal toilet usage for a family of 4 (2 men, 2 women; based on consumer habits and practices research). The sequence of 40 total flushes consists of 14 flushes with an empty bowl; 8 flushes with tissue only; 6 flushes with tissue and package; 6 flushes with tissue, absorbent article and package; and 6 flushes with tissue and simulated fecal matter (SFM). When testing the package and absorbent article as a combination, perform routines 1 and 2 using both the package and the absorbent article placed individually into the bowl by first removing the absorbent article from the package. The SFM, when it is used, is placed in the bowl just prior to the addition of tissue. The SFM loading of 160 g±5 g consists of two 1 inch (2.5 centimeter)×4 inch (10 centimeter) pieces and one 1 inch (2.5 centimeter)×2 inch (5 centimeter) piece. Folded tissue strips are placed in the bowl at 10 second intervals. Ten seconds after the final strip of tissue, the absorbent article or package is placed into the bowl, the toilet is flushed. The flushing sequence is described below as a series of two routines combined in the following order:

Routine #1 (To be performed first 6 times for a total of 36 flushes)

1) Flush With Tissue Only—Take a drain line blockage reading 2 minutes after the water reaches the simulated obstruction, the snag point, wait 1 additional minute, and move to step 2.

2) Flush With Empty Bowl. Take a drain line blockage reading 2 minutes after the water reaches the snag point and move to step 3.

3) Flush With Tissue and Package—Take a drain line blockage reading 2 minutes after the water reaches the snag point, wait 1 additional minute, and move to step 4.

4) Flush With Tissue and Absorbent Article and Package—Take a drain line blockage reading 2 minutes after the water reaches the snag point, wait 1 additional minute, and move to step 5.

5) Flush With Empty Bowl. Take a drain line blockage reading 2 minutes after the water reaches the snag point and move to step 6.

6) Flush With Tissue and Simulated Fecal Matter (SFM). Take a drain line blockage reading 2 minutes after the water reaches the snag point, wait 1 additional minute.

Routine #2 (To be performed 1 time for a total of 4 flushes)

1) Flush With Tissue Only—Take a drain line blockage reading 2 minutes after the water reaches the snag point, wait 1 additional minute, and move to step 2.

2) Flush With Empty Bowl. Take a drain line blockage reading 2 minutes after the water reaches the snag point and move to step 3.

3) Flush With Tissue Only—Take a drain line blockage reading 2 minutes after the water reaches the snag point, wait 1 additional minute, and move to step 4.

4) Flush With Empty Bowl. Take a drain line blockage reading 2 minutes after the water reaches the snag point.

Total number of flushes for the sequence (Routine 1+Routine 2) is 40.

If, after the second flush in the flushing sequence, the product remains in the bowl or trap after flushing, the tissue and or absorbent article and or package is plunged into the drainage line manually and the flushing sequence will continue. After completion of each trial loading, the drainage pipe will be cleared prior to beginning subsequent testing.

The above described flushing sequence is repeated three times for each test product.

Data Reporting

The degree of drain line blockage is determined by measuring the length of water dammed up behind the obstruction. Graduations are marked every 12 inches (30 centimeters) on the drainpipe upstream of the obstruction. Each one foot length that the water is backed up corresponds to 0.25 inch (0.6 centimeter) or 6.25% of blockage at the obstruction point. Test product residues which exit the drainpipe are also collected.

The following data are recorded for each evaluation:

1) Incidence of failure (%) of package to clear bowl and trap in one flush

2) Incidence of failure (%) of package to clear bowl and trap in two flushes

3) Incidence of package on simulated snag

4) Maximum level (%) of drain line blockage

5) Cumulative level (%) of drain line blockage over the 2 day simulated test period.

Preferably, the package described herein will completely clear the bowl at least about 70% of the time in two or fewer flushes, more preferably at least about 80% of the time in one flush, and most preferably at least about 95% of the time in one flush. The package described herein will preferably have a maximum level of drain line blockage of less than or equal to about 80%. The package described herein will preferably have a cumulative level of drain line blockage over the 2 day simulated test period of less than or equal to about 50%.

Preparation of Synthetic Fecal Material

I. Materials Needed:

Feclone synthetic fecal matter (900 grams);
(Available from Siliclone Studio, Valley Forge, Pa. as product BFPS-7 dry concentrate)
Tap water at 100° C. (6066 grams)

II. Equipment Needed:

Mixer (Available from Hobart Corp., Troy, Ohio as Model A200)
Extruder (Available from Hobart Corp., Troy, Ohio as Model 4812)
Disposable Centrifuge tubes with screw caps (50 ml) (Available from VWR Scientific, Chicago, Ill. as Catalog No. 21-008-176)
Water Bath to control temperature to 37° C.

III. Preparation:

1. Pour the 100° C. water into the mixing bowl of the mixer and add the dry Feclone concentrate.
2. Mix on low for 1 minute.
3. Mix on medium speed for 2 minutes.
4. After the material is well mixed, transfer to the extruder.
5. Using an ice pick, punch a small hole in the tip of each centrifuge tube.
6. Extrude the Feclone into the centrifuge tubes.
7. Cap the centrifuge tubes and store in the refrigerator.
8. Before using, put the tubes in the water bath at 38° C.

| Water Dispersion Test | |
|---|---|
| Apparatus | |
| Stirrer | Magnetic, Thermolyne type Model S7225 or 7200. Permanently inscribe a circle 3.5 inches (8.9 centimeter) on the top surface of the stirrer. The center of the circle must be coincident with the geometric center of the stirrer. |
| Stirring Bar | 2.5 inch (6.2 centimeter) TEFLON coated with spinning ring. Permanently mark one end of the bar with black ink for a distance of 0.5 inch (1.2 centimeter) back from the tip. |
| Thermometer | 30 to 120° F. with 1 degree divisions |
| Timer | Digital stopwatch |
| Stroboscope | Variable speed stroboscope, model 964 available from Strobette, Power Instrument, Inc. of Skokie, IL is suitable |
| Beaker | Kimax brand 2000 milliliter with spout with a diameter at the base of 135 ± 2 mm and a height at the 2000 ml mark of 162 ± 2 mm, Inscribe a fill mark at a height of 5.6 inches (14.3 centimeters) from the flat bottom of the beaker. Do not use any beaker not having a flat bottom. |

| -continued | |
|---|---|
| Water Dispersion Test | |
| Conditioned Room | Temperature and humidity should be controlled to remain within the following limits:<br>Temperature: 73 ± 3° F. (23° C. ± 2° C.)<br>Humidity: 50 ± 2% Relative Humidity |
| Test Setup | |
| 1. | Fill the beaker to the fill mark with 73 ± 3° F. (23° C. ± 2° C.) tap water. |
| 2. | Place the beaker on the magnetic stirrer centering it in the inscribed circle. |
| 3. | Add the stirring bar to the beaker. |
| 4. | Turn the stroboscope on and set the speed to 1000 rpm according to the manufacturer's directions. |
| 5. | Turn the magnetic stirrer on with the on/off switch. Adjust the speed of the magnetic stirrer until the stirring bar appears to be stationary and both ends appear to be black. This indicates that the magnetic stirrer is turning at 500 rpm (i.e. half the setting on the stroboscope). Turn the magnetic stirrer off with the on/off switch. |
| Procedure | |
| 1. | Hold a sample (e.g. an absorbent article, such as an absorbent interlabial device or package) 3 to 4 inches (7.6 to 10.2 centimeters) above the surface of the water. Gently drop the sample onto the water surface, starting the timer when the sample touches the water surface. Wait 5 seconds. |
| 3. | Start the magnetic stirrer with the on/off switch. If the sample disrupts the rotation of the stirring bar, stop the stirrer, re-orient the bar, and immediately start the stirrer again. |
| 4. | Record the time required until the sample separates into at least two pieces. Separation does not include the disassociation of a few individual fibers from an otherwise intact sample. The time is the total time the sample is immersed in the water including the time the stirrer may have been stopped to re-orient the sample.<br>A circular wire screen, consisting of an outer circle of 3" (7.62 cm) diameter and equally divided into 6 sections made from copper wire about 1 mm in diameter, may be placed immediately suspended above the stir bar in cases where the package substantially disrupts the rotation of the stir bar.<br>If the package repeatedly causes substantial disruption to the rotation of the stirring bar, the package may be suspended by a string attached to the package via a clamp attached to the package ⅜" (.95 cm) from the edge of the package, and then suspending the lowest end of the package 1" above the stir bar. |
| 5. | Repeat steps 1 through 4 with an additional 3 samples. |

Calculation and Reporting

Calculate and report the mean and standard deviation of the water dispersibility time for the four samples tested. Preferably, the package will disperse into at least two fragments in less than or equal to about two hours.

Wet-Out Time

Purpose:

To determine the amount of time for a package to become completely wet by either absorbing the liquid or sinking below the surface of the liquid. Conventional packages tend to stay afloat, and if they are flushed, whether they are designed to be or not, are typically pulled below the surface of the liquid by the force of the water when the toilet is flushed.

1. Hold the absorbent article, such as the interlabial device or package 3 to 4 inches (7.62 to 10.16 cm) above the surface of distilled water.

2. Gently drop the sample onto the water surface, so that the broad surface of the package strikes the surface. Start timing.

3. Stop timing when the sample is completely wet.

4. Repeat steps 1–3 for five samples.

Report a mean and standard deviation for the wet-out time. The wet-out time is preferably less than or equal to 30 seconds and more preferably less than or equal to 15 seconds.

28 Day Sludge Test

Purpose:

To determine the extent to which a package disintegrates upon exposure to biologically active anaerobic sludge. Anaerobic conditions are typically found in household septic tanks, as well as in municipal sewage treatment facilities in the form of anaerobic sludge digesters. Test products, such as the package are combined with anaerobic digester sludge to determine the extent and rate of disintegration of test products over a 28 day period. Disintegration (as measured by weight change) is typically measured on days 3, 7, 14, 21 and 28 of the particular study. This protocol is modeled after the National Sanitation Foundation, Ann Arbor, Michigan, International Protocol: Evaluation of the Anaerobic Disintegration of a Test Product, November, 1992.

Materials:

Control Product

Tampax brand tampons will be used as a positive control product in the anaerobic disintegration test.

Material Preparation

Prior to the addition of the test and control products to the reactors, the materials will be dried in a hot air oven at 103°±2° C. for 2 hours and then weighed to determine the initial weight. Approximately equal weights of the control and test products will be placed in respective reactors.

Anaerobic Sludge:

The sludge used in this evaluation will be anaerobic sludge obtained from a municipal waste water treatment plant, or raw sewage obtained as influent from a waste water treatment plant that has been concentrated by settling and decanting the overlying water. Prior to use in the evaluation, the following parameters of the sludge will be measured in accordance with standard laboratory operating procedures:

Total solids

Total volatile solids pH

The sludge should meet the following criteria for use in the evaluation:

pH between 6.5 and 8

Total solids≧15,000 mg/L

Total volatile solids≧10,000 mg/L

The criteria for the activity of the sludge requires that the control tampon material must lose at least 95% of its initial dry weight after 28 days exposure.

Procedure:

The test and control products are added to a 2L wide mouth glass flask (reactor) containing 1500 ml of anaerobic digester sludge or concentrated raw sewage. Three reactor flasks per test material per sampling day are prepared. Thus, if disintegration is measured on days 3, 7, 14, 21, and 28, there will be a total of 15 reactor flasks for the test product and 15 flasks for the control product. The reactors are sealed and placed in an incubator maintained at 35±2° C. On the specified sampling days, three reactors each for the test and control material are removed from the incubator. On the designated sample days, the contents of each reactor will be passed through a 1 mm mesh screen to recover any undisintegrated material. Any collected material will be rinsed with tap water, removed from the screen and placed in a hot air oven at 103±2° C. for at least 2 hours. The dried material will be weighed to determine final weight. Visual observations of the physical appearance of the materials when recovered from the reactors will also be made and recorded.

Results:

The rate and extent of anaerobic disintegration of each test material and the control material is determined from initial dry weights of the material and the dried weights of the material recovered on the sampling days. The percent anaerobic disintegration is determined using the following equation (percent weight loss):

$$\text{Percent Disintegration} = \frac{(\text{initial dry weight} - \text{final dry weight})}{(\text{initial dry weight})} \times 100$$

The average percent disintegration for the test and control products for each sampling day will be presented. For the purposes of the appended claims, the percent disintegration values are for day 28 of the study.

The disclosures of all patents, patent applications (and any patents which issue thereon, as well as any corresponding published foreign patent applications), and publications mentioned throughout this patent application are hereby incorporated by reference herein. It is expressly not admitted, however, that any of the documents incorporated by reference herein teach or disclose the present invention. It is also expressly not admitted that any of the commercially available materials or products described herein teach or disclose the present invention.

What is claimed is:

1. A re-sealable individual package in combination with an absorbent interlabial device, comprising:

a) a package having a longitudinal axis, a top portion, a bottom portion positioned oppositely to the top portion, a first surface and a second surface, the first surface being the internal surface and the second surface being the external surface, the package being folded about the longitudinal axis to form two halves, the package being sealed on at least three sides, at least one sealed side of the package being re-sealable, one-half of the internal surface of the folded package facing toward the other half of the internal surface of the folded package; and b) an absorbent interlabial device being positioned between the package halves, the absorbent interlabial device having a longitudinal axis, an absorbent portion having a first surface and a second surface, the absorbent interlabial device being readily retrievable from the package such that a user neither touches nor contaminates the first surface of the absorbent portion of the absorbent interlabial device with any part of a user's hand, the absorbent interlabial device further comprising a contaminant impermeable portion attached to the second surface of the absorbent portion of the absorbent interlabial device, the package comprising a grasping portion attached to the contaminant impermeable portion of the absorbent interlabial device, the grasping portion being grasped by a user to remove the absorbent interlabial device from the re-sealable individual package.

2. The re-sealable individual package for an absorbent interlabial device of claim 1 wherein the first surface of the absorbent portion further comprises a topsheet.

3. The re-sealable individual package for an absorbent interlabial device of claim 1 wherein the contaminant impermeable portion of the absorbent interlabial device at last partially covers the fingers on the user's hand grasping the grasping portion to remove the absorbent interlabial device from the re-sealable individual package.

4. The re-sealable individual package for an absorbent interlabial device of claim 1 wherein the length and width dimensions of the contaminant impermeable portion are greater than the length and width dimensions of the absorbent portion of the absorbent interlabial device.

5. The re-sealable individual package for an absorbent interlabial device of claim 1 wherein the absorbent interlabial device is positioned within the re-sealable individual package such that the absorbent interlabial device is folded about the longitudinal axis of the absorbent interlabial device, the absorbent portion of the first surface of the absorbent interlabial device being held adjacent to the internal surface of the re-sealable individual package.

6. The re-sealable individual package for an absorbent interlabial device of claim 1 wherein at least one side of the re-sealable individual package may be re-sealed once the absorbent interlabial device is removed from the re-sealable individual package.

7. The re-sealable individual package for an absorbent interlabial device of claim 6 wherein the absorbent interlabial device is placed back into the package after the absorbent interlabial device is used, the re-sealable individual package being re-sealed with the used absorbent interlabial device being positioned therein.

8. The re-sealable individual package for an absorbent interlabial device of claim 6 wherein the re-sealable individual package is sealed on at least one side by a re-sealing member.

9. The re-sealable individual package for an absorbent interlabial device of claim 8 wherein the re-sealing member is positioned at least partially on the top portion of the re-sealable individual package.

10. The re-sealable individual package for an absorbent interlabial device of claim 9 wherein the re-sealing member is positioned on one of the halves of the internal surface of the re-sealable individual package.

11. The re-sealable individual package for an absorbent interlabial device of claim 10 wherein the re-sealing member is positioned on both of the halves of the internal surface of the re-sealable individual package.

12. The re-sealable individual package for an absorbent interlabial device of claim 8 wherein the re-sealing member is selected from the group consisting of re-fastenable tape, thermal bonds, pressure sensitive tapes, pressure sensitive glues and combinations thereof.

13. The re-sealable individual package for an absorbent interlabial device of claim 12 wherein the re-sealable individual package further comprises a disruptive member for opening the re-sealable individual package.

14. The re-sealable individual package for an absorbent interlabial device of claim 13 wherein the disruptive member is positioned adjacent to the top portion of the re-sealable individual package.

15. The re-sealable individual package for an absorbent interlabial device of claim 14 wherein the disruptive member extends partially along the top portion of the re-sealable individual package.

16. The re-sealable individual package for an absorbent interlabial device of claim 14 wherein the disruptive member extends substantially along the top portion of the re-sealable individual package.

17. The re-sealable individual package for an absorbent interlabial device of claim 13 wherein the disruptive member comprises an opening device.

18. The re-sealable individual package for an absorbent interlabial device of claim 17 wherein the opening device comprises a pull-string.

19. The re-sealable individual package for an absorbent interlabial device of claim 17 wherein the opening device comprises perforations.

20. The re-sealable individual package for an absorbent interlabial device of claim 1 wherein the absorbent interlabial device is flushable.

21. The re-sealable individual package for an absorbent interlabial device of claim 1 wherein the absorbent interlabial device is biodegradable.

22. The re-sealable individual package for an absorbent interlabial device of claim 1 wherein the package is flushable.

23. The re-sealable individual package for an absorbent interlabial device of claim 1 wherein the package is biodegradable.

24. A re-sealable individual package in combination with an absorbent interlabial device, comprising:
   a) a package comprising two attached sheets, a longitudinal axis, a top portion, a bottom portion positioned oppositely to the top portion, a first surface and a second surface, the first surface being the internal surface and the second surface being the external surface, the package being substantially sealed about the longitudinal axis and sealed on at least three sides, at least one sealed side of the package being re-sealable, the internal surface further comprising a first internal surface and a second internal surface facing toward the first internal surface; and
   b) an absorbent interlabial device being positioned in the package, the absorbent interlabial device having a longitudinal axis, an absorbent portion having a first surface and a second surface, the absorbent interlabial device being readily retrievable from the package such that a user neither touches nor contaminates the first surface of the absorbent portion of the absorbent interlabial device with any part of a user's hand, the absorbent interlabial device further comprising a contaminant impermeable portion attached to the second surface of the absorbent portion of the absorbent interlabial device, the package comprising a grasping portion attached to the contaminant impermeable portion of the absorbent interlabial device, the grasping portion being grasped by a user to remove the absorbent interlabial device from the re-sealable individual package.

* * * * *